US008454950B2

(12) United States Patent
Haschke et al.

(10) Patent No.: US 8,454,950 B2
(45) Date of Patent: Jun. 4, 2013

(54) MATERNAL SUPPLEMENT

(75) Inventors: Ferdinand Haschke, La Tour-de-Peilz (CH); Zdenek Kratky, New Milford, CT (US)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/269,284

(22) Filed: Oct. 7, 2011

(65) Prior Publication Data

US 2012/0027738 A1 Feb. 2, 2012

Related U.S. Application Data

(62) Division of application No. 12/301,723, filed as application No. PCT/EP2007/054916 on May 22, 2007.

(30) Foreign Application Priority Data

May 23, 2006 (EP) .................................. 06114360

(51) Int. Cl.
*A01N 63/00* (2006.01)
*A01N 65/00* (2009.01)
*C12N 1/20* (2006.01)

(52) U.S. Cl.
USPC ........................ 424/93.5; 424/93.1; 435/252.9

(58) Field of Classification Search
None
See application file for complete search history.

(56) References Cited

U.S. PATENT DOCUMENTS

| | | | |
|---|---|---|---|
| 2002/0102330 A1 * | 8/2002 | Schramm et al. | 426/72 |
| 2003/0050341 A1 * | 3/2003 | Bydlon et al. | 514/560 |
| 2003/0108594 A1 * | 6/2003 | Manning et al. | 424/439 |
| 2003/0118571 A1 * | 6/2003 | Reid et al. | 424/93.45 |
| 2006/0088574 A1 * | 4/2006 | Manning et al. | 424/439 |

FOREIGN PATENT DOCUMENTS

| | | |
|---|---|---|
| SU | 2093996 | 1/1992 |
| WO | 9212711 | 6/1992 |
| WO | WO 9953777 A1 * | 10/1999 |
| WO | WO 0239835 A1 * | 5/2002 |
| WO | 2004012727 | 2/2004 |
| WO | 2005039319 | 5/2005 |
| WO | 2005115341 | 12/2005 |
| WO | WO 2006108824 * | 10/2006 |

OTHER PUBLICATIONS http://web.archive.org/web/20040804215656/http://www.nutristrategy.com/nutrition/calories.htm—web archived version from Aug. 4, 2004.*

* cited by examiner

*Primary Examiner* — Chris R Tate
*Assistant Examiner* — Douglas White
(74) *Attorney, Agent, or Firm* — K&L Gates LLP

(57) ABSTRACT

The use of docosahexaenoic acid in the manufacture of a composition for administration to a pregnant woman for reducing the risk of development of overweight or obesity of the baby in infancy and/or early childhood.

8 Claims, No Drawings

MATERNAL SUPPLEMENT

CROSS-REFERENCE TO RELATED APPLICATIONS

This application is a divisional of U.S. Pat. application Ser. No. 12/301,723, filed Nov. 20, 2008, which is the U.S. national stage designation of International application No. PCT/EP2007/054916 filed May 22, 2007, which claims priority to EP 06114360.8, filed on May 23, 2006, the entire contents of which are expressly incorporated herein by reference.

FIELD OF THE INVENTION

This invention relates to a nutritional supplement for pregnant women to reduce the risk of obesity of the baby in later life.

BACKGROUND TO THE INVENTION

Scientific literature suggests that supplementation of infant formula with the long chain polyunsaturated fatty acids (LC-PUFA) docosahexaenoic acid (DHA, omega 3) and arachidonic acid (ARA, omega 6) may have many health benefits for the infant. Indeed it has been demonstrated that in pre-term infants receiving DHA and ARA either from breast milk or infant formula containing these LC-PUFA demonstrate improved cognitive abilities, visual acuity and motor skills when compared with unsupplemented pre-term infants. The picture for term infants is less clear. Some studies have been published showing similar benefits of supplementation to those demonstrated with pre-term infants but other studies have found no effect of supplementation.

It has been suggested that these conflicting results with term infants could be due to the influence of maternal LC-PUFA status. DHA in particular is accumulated preferentially to other fatty acids by the foetus in the last trimester of pregnancy. In premature birth, this period does not last the full three months and it may be expected that the response of the pre-term infant to supplementation with DHA would be marked. A term infant, however, would have the benefit of maternal supply during the last three months of gestation and, assuming that supply to be adequate, could be expected to have adequate or near adequate DHA status at birth.

However, in the developed world at least, there are increasing concerns over the physiological effects of a diet rich in saturated fats and favouring the precursors of omega 6 LC-PUFA such as ARA at the expense of the precursors of omega 3 LC-PUFA such as DHA on the physiological omega 6:omega 3 ratio in general. In particular, there are concerns that pregnant women eating a normal Western diet may not be able to supply sufficient omega 3 precursors to meet the developing foetus's need to synthesise DHA. For this reason it has been proposed for example in WO 2003/017945 to develop a range of supplements for pregnant women containing DHA with ARA and various vitamins and minerals. It is claimed that taking such supplements could benefit the health of both mother and baby. Examples of possible benefits to the unborn baby are stated to include optimised growth and development of the nervous system and improved foetal weight gain.

The prevalence of obesity in adults, adolescents and children has increased rapidly and research to identify approaches to prevent overweight and obesity in childhood is considered to be of major public health importance. Overweight and obesity in childhood is a relatively recent phenomenon that already affects over 15 million children under age 5 across the world. Almost 30% of adolescents and children in the US and between 10 and 30% of children in Europe may be classified as overweight or obese. It has been suggested that rapid growth during the first four months of life may be associated with the development of overweight or obesity later in life and that the rate of weight gain in the first few weeks of life may be particularly important.

Recently, attention has focused on the possible role of LC-PUFA in the development and treatment of overweight and obesity. For example, WO 2004/012727 discloses a method for decreasing the appetite of a mammal comprising enterally administering an omega 3 LC-PUFA to the mammal. Ruzickova J. et al. (Lipids. 2004 December; 39(12): 1177-85) document augmentation of the antiadipogenic effect of EPA/DHA during development of obesity and suggest that EPA/DHA could reduce accumulation of body fat by limiting both hypertrophy and hyperplasia of fat cells.

However, Lauritzen L. et al. (Maternal fish oil supplementation in lactation and growth during the first 2.5 years of life. Pediatr Res. 2005 August; 58(2):235-42) performed a randomized trial on mothers after delivery. The women were randomly assigned to take a supplement of fish oil (rich in omega 3 LC-PUFA such as DHA) or olive oil. The supplement was taken during 0 to 4 months of lactation. 122 children were studied of whom 70 were followed up until 30 months. The BMI of the children was measured at birth and at 2, 4, 9 and 30 months of age. The results showed that the BMI of infants in the fish oil group was higher than the BMI of infants in the olive oil group from the age of 9 months on.

There remains a need to provide alternative methods to address the risk of overweight and obesity, particularly during childhood.

SUMMARY OF THE INVENTION

The inventors have conducted a study investigating the effect of a daily oral supplement containing DHA on red blood cell phospholipid DHA concentration in pregnant women at 37 weeks of gestation and whether a daily oral intake of DHA influences the DHA concentrations in breast-milk or/and red blood cell phospholipids in mother and/or infant during lactation. During this study, it was surprisingly found that the weight and body mass index of children in the DHA supplemented group at age 21 months were significantly lower than the weight and body mass index of children in the group not receiving DHA.

Accordingly, in a first aspect the present invention provides the use of docosahexaenoic acid in the manufacture of a composition for administration to a pregnant woman in at least the third trimester of pregnancy and, after delivery, to the newborn baby for a period not exceeding three months for reducing the risk of development of overweight or obesity of the baby in infancy and/or early childhood.

In a second aspect, the present invention provides the use of docosahexaenoic acid in the manufacture of a composition for administration to a pregnant woman for reducing the risk of development of overweight or obesity of the baby in infancy and/or early childhood.

In a third aspect, the present invention provides the use of docosahexaenoic acid in the manufacture of a composition for administration to a pregnant women to promote the development of lean body mass of the baby in infancy and/or early childhood.

The invention extends to a method of reducing the risk of obesity of a baby in infancy and/or early childhood by providing to a pregnant woman in need thereof a composition containing a therapeutic amount of docosahexaenoic acid.

The invention further extends to a method of promoting the development of lean body mass of a baby in infancy and/or early childhood by providing to a pregnant woman in need thereof a composition containing a therapeutic amount of docosahexaenoic acid.

If supplementation with DHA is continued after delivery, the composition may either be administered to the infant via the breast feeding mother or may be administered directly to the infant.

DETAILED DESCRIPTION OF THE INVENTION

In this specification, the following terms have the following meanings:—

"body mass index" or "BMI" means the ratio of weight in Kg divided by the height in metres, squared.

"infancy and early childhood" means the first six years of life

"overweight" is defined as having a BMI between 25 and 30

"obese" is defined as having a BMI greater than 30

All references to percentages are percentages by weight unless otherwise stated.

The daily dose of DHA for a pregnant woman is preferably between 100 and 500 mg, more preferably between 200 and 400 mg. The amount of DHA in the composition may thus be selected accordingly depending upon whether it is intended to be consumed once a day or more frequently. For example, a composition intended to be consumed once a day may contain 200 mg of DHA.

Suitable sources of DHA include fish oil and biomass obtained from the culture of a suitable micro-organism such as *Crypthecodium cohnii*. The composition is preferably taken throughout pregnancy to build up maternal stores of DHA although supplementation in the second and more particularly the third trimesters is believed to be particularly advantageous. Likewise supplementation may continue after birth either via continued consumption of the composition by the mother if the baby is to be breast fed or by administering DHA to the baby, for example by including DHA in the infant formula used to feed the baby. A suitable DHA content in infant formula ranges between 0.2 and 0.8% by weight of total fatty acids in the formula.

In one embodiment, the composition is a nutritional composition. The composition may be a nutritionally complete formula, a nutritional supplement, a food product such as a dairy product, a chilled or shelf stable beverage or a soup, a dietary supplement, a meal replacement, or a nutritional bar for example.

A nutritionally complete formula for use according to the invention may comprise a source of protein. Any suitable dietary protein may be used for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred. The composition may also contain a source of carbohydrates and a source of fat.

If the formula includes a fat source in addition to the DHA, the fat source preferably provides 5% to 40% of the energy of the formula; for example 20% to 30% of the energy. A suitable fat profile may be obtained using a blend of canola oil, corn oil and high-oleic acid sunflower oil.

A source of carbohydrate may be added to the formula. It preferably provides 40% to 80% of the energy of the formula.

Any suitable carbohydrate may be used, for example sucrose, lactose, glucose, fructose, corn syrup solids, maltodextrins, and mixtures thereof. Dietary fibre may also be added if desired. Dietary fibre passes through the small intestine undigested by enzymes and functions as a natural bulking agent and laxative. Dietary fibre may be soluble or insoluble and in general a blend of the two types is preferred. Suitable sources of dietary fibre include soy, pea, oat, pectin, guar gum, gum Arabic, fructooligosaccharides, galacto-oligosaccharides, sialyl-lactose and oligosaccharides derived from animal milks. A preferred fibre blend is a mixture of inulin with shorter chain fructo-oligosaccharides. Preferably, if fibre is present, the fibre content is between 10 and 40 g/l of the formula as consumed. The formula may also contain minerals and micronutrients such as trace elements and vitamins in accordance with the recommendations of Government bodies such as the USRDA. For example, the formula may contain per daily dose one or more of the following micronutrients in the ranges given: —300 to 500 mg calcium, 50 to 100 mg magnesium, 150 to 250 mg phosphorus, 5 to 20 mg iron, 1 to 7 mg zinc, 0.1 to 0.3 mg copper, 50 to 200 µg iodine, 5 to 15 µg selenium, 1000 to 3000 µg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 µg Vitamin B12, 100 to 800 µg folic acid, 30 to 70 µg biotin, 1 to 5 µg Vitamin D, 3 to 10 IU Vitamin E.

A probiotic bacterial strain may be added to the formula. One example of a suitable strain is *Lactobacillus rhamnosus* CGMCC 1.3724.

One or more food grade emulsifiers may be incorporated into the formula if desired; for example diacetyl tartaric acid esters of mono- and di-glycerides, lecithin and mono- and di-glycerides. Similarly suitable salts and stabilisers may be included.

The formula is preferably enterally administrable; for example in the form of a powder or a liquid concentrate for re-constitution with milk or water, a solid product or a ready-to-drink beverage.

The formula may be prepared in any suitable manner. For example, it may be prepared by blending together the protein, the carbohydrate source, and the fat source including the DHA in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenised; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger; for example a plate heat exchanger.

Then, the liquid mixture may be cooled to about 60° C. to about 85° C.; for example by flash cooling. The liquid mixture may then be again homogenised; for example in two stages at about 10 MPa to about 30 MPa in the first stage and about 2 MPa to about 10 MPa in the second stage. The homogenised mixture may then be further cooled to add any heat sensitive components; such as vitamins and minerals. The pH and solids content of the homogenised mixture are conveniently adjusted at this point.

If it is desired to produce a powdered formula, the homogenised mixture is transferred to a suitable drying apparatus such as a spray drier or freeze drier and converted to powder. The powder should have a moisture content of less than about 5% by weight.

If it is desired to produce a liquid formula, the homogenised mixture is preferably aseptically filled into suitable containers by pre-heating the homogenised mixture (for example to about 75 to 85° C.) and then injecting steam into the homogenised mixture to raise the temperature to about 140 to 160° C.; for example at about 150° C. The homogenised mixture may then be cooled, for example by flash cooling, to a temperature of about 75 to 85° C. The homogenised mixture may then be homogenised, further cooled to about room temperature and filled into containers. Suitable apparatus for carrying out aseptic filling of this nature is commercially available. The liquid composition may be in the form of a ready to feed formula having a solids content of about 10 to about 14% by weight or may be in the form of a concentrate; usually of solids content or about 20 to about 26% by weight.

In another embodiment, a conventional food product such as a yoghurt, or a breakfast cereal may be enriched with the DHA.

In yet a further embodiment, a supplement containing DHA in an amount sufficient to achieve the desired effect in an individual can be prepared. This supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. The supplement may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or enteral administration as well as vitamins, minerals trace elements and other micronutrients in accordance with the recommendations of Government bodies such as the USRDA. For example, the supplement may contain one or more of the following micronutrients in the ranges given: —300 to 500 mg calcium, 50 to 100 mg magnesium, 150 to 250 mg phosphorus, 5 to 20 mg iron, 1 to 7 mg zinc, 0.1 to 0.3 mg copper, 50 to 200 μg iodine, 5 to 15 μg selenium, 1000 to 3000 μg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 μg Vitamin B12, 100 to 800 μg folic acid, 30 to 70 μg biotin, 1 to 5 μg Vitamin D, 3 to 10 IU Vitamin E.

The invention will now be further illustrated by reference to the following examples: —

EXAMPLE 1

An example of a shelf stable liquid nutritional supplement to be used according to the present invention is as follows: —

|  | Per 100 kcal | Per 100 g ready to drink | Per serving (190 ml) |
| --- | --- | --- | --- |
| Energy (kcal) | 100 | 65 | 130 |
| Fat (g) | 0.92 | 0.60 | 1.20 |
| DHA (mg) (from fish oil) | 200 | 130 | 260 |
| Protein (g) | 3.54 | 2.30 | 4.60 |
| Carbohydrate (g) | 19.4 | 12.60 | 25.2 |
| Dietary fibre (g) | 3.62 | 2.35 | 4.70 |
| Minerals |  |  |  |
| Sodium (mg) | 51 | 33 | 66 |
| Potassium (mg) | 238 | 155 | 310 |
| Chloride (mg) | 123 | 80 | 160 |
| Calcium (mg) | 308 | 200 | 400 |
| Phosphorus (mg) | 162 | 105 | 210 |
| Magnesium (mg) | 58.0 | 38 | 76 |
| Selenium (μg) | 7.7 | 5.0 | 10.0 |
| Vitamins |  |  |  |
| Beta carotene (μg) | 1600 | 1050 | 2100 |
| Vitamin D (μg) | 3.8 | 2.50 | 5.0 |
| Vitamin E (IU) | 4.6 | 3.0 | 6.0 |
| Vitamin C (mg) | 38 | 25 | 50 |
| Vitamin B1 (mg) | 1.2 | 0.75 | 1.5 |
| Vitamin B2 (mg) | 1.3 | 0.85 | 1.7 |
| Niacin (mg) | 12 | 8 | 16 |
| Vitamin B6 (mg) | 1.1 | 0.7 | 1.4 |
| Folic acid (μg) | 310 | 200 | 400 |
| Vitamin B12 (μg) | 1.2 | 0.75 | 1.5 |
| Biotin (μg) | 54 | 35 | 70 |
| Trace Elements |  |  |  |
| Iron (mg) | 12 | 7.5 | 15 |
| Iodine (μg) | 150 | 100 | 200 |
| Copper (mg) | 0.20 | 0.13 | 0.26 |
| Zinc (mg) | 3.8 | 2.5 | 5.0 |

EXAMPLE 2

This example compares the effect of administering a nutritional supplement including DHA to pregnant women with the effect of administration of the same supplement but without the DHA to a comparable group of pregnant women on the evolution of weight and body mass of their children.

A randomised, controlled, double blind, single centre clinical trial was carried out at Klinik fair Geburtsmedizin, Charité, Campus Virchow Klinikum, Berlin, Germany. The study was carried out according to the principles and rules laid down in the Declaration of Helsinki (as amended). A total of 144 healthy adult Caucasian non-smoking women in the $20^{th}$ to $22^{nd}$ week of pregnancy willing to breastfeed for at least 3 months were recruited and assigned to one of three treatment groups. Subjects in all three groups received a daily nutritional supplement with the only difference being the content of the supplement as follows: —

Group 1: Supplement (Vitamins, Minerals)
Group 2: Supplement (Vitamins, Minerals+prebiotic)
Group 3: Supplement (Vitamins, Minerals+prebiotic+ DHA as per Example 1)

All supplements were in the form of a shelf-stable liquid containing per serving 4.6 g protein and 25 g carbohydrate, vitamins and minerals. In addition, the supplement for Groups 2 and 3 contained 3.8 g per serving of a mixture of short and long chain facto-oligosaccharides produced by the hydrolysis of inulin and the supplement for Group 3 contained 0.26 g per serving DHA. 190 ml of the supplement was taken per day in all groups delivering 120 kcal for Groups 1 and 2 and 130 kcal for Group 3. The supplement was taken for the remainder of the pregnancy and for the first three months of lactation.

All supplements were supplied to the hospital blinded and distinguishable only by three different colours of the label. The colour code was known only to the manufacturer.

Daily consumption of the supplements was recorded by the subjects in a booklet. Compliance was checked every six weeks by telephone call and the consumption record was brought to the hospital at each visit. No other nutritional supplements were taken during the study period.

Inter alia, the following outcomes were measured: — red blood cell phospholipid DHA concentration in pregnant women at week 37 of pregnancy and in babies at 1 and 3 months of age;

DHA concentration in breastmilk of lactating mothers three months after birth; Anthropometric values (length, weight, BMI and head circumference) of the babies at one, three and twenty-one months of age.

Of the 144 pregnant women enrolled in the trial, 116 babies remained in the study until the age of 3 months and 69 until the age of 21 months.

It was found that the DHA concentration as a % of total fatty acids at 3 months in breastmilk in Group 1 subjects was 0.25 (+/−0.10) compared to 0.26 (+/−0.13), and 0.50 (+/−0.19) in Group 2 and Group 3 subjects, respectively. The treatment effect was significant in Group 3 compared to Groups 1 and 2. The red blood cell DHA concentration (% of total fatty acids) at 3 months in babies in Group 1 was 7.49 (+/−2.00) compared to 6.88 (+/−2.76) in Group 2, and 9.79 (+/−2.21) in Group 3. Again, the treatment effects were significantly different. Furthermore, the omega 6:omega 3 ratio in the red blood cells of the women in Groups 1 and 2 was 2:1 compared to 1.55:1 for the women in Group 3. Likewise, the omega 6:omega 3 ratio in breastmilk of the women in Groups 1 and 2 was also 2:1 compared to 0.85:1 for the women in Group 3 and the omega 6:omega 3 ratio in the red blood cells of the babies in Groups 1 and 2 at 3 months of age was 2.4:1 compared to 1.6:1 for the babies of women in Group 3 at the same age.

At birth, anthropometric values were nearly identical in all groups. But a significant time dependent effect was observed for babies from Group 3 in weight (p=0.049) and BMI (p=0.044), when taking into account sex, gestational and chronological age of the baby, the mother's education, parity, BMI, gestational weight gain and breast feeding. After controlling for all influential variables, 21 month old children from Group 3 were found to have a significantly lower weight (0.6 kg less, p=0.006) and BMI (0.77 less, p=0.031) than children in Groups 1 and 2 while head circumference was slightly larger in Group 3 and length was similar in all groups.

As body length is a recognised indicator for lean body mass, it can therefore be said that children from Group 3 having a lower weight and BMI than children from Groups 1 and 2 but similar length have a leaner body mass than children from Groups 1 and 2.

The invention claimed is:

1. A method for reducing the risk of development of overweight or obesity of a baby in infancy and/or early childhood, the method comprising administering a daily dose of a composition comprising 100 to 500 mg of docosahexaenoic acid to a pregnant woman in need thereof, wherein the composition comprises a fat source that provides 5 % to 40 % of the energy of the composition and a carbohydrate source that provides 40 % to 80 % of the energy of the composition, the composition further comprising an effective amount of a mixture of short and long chain fructo-oligosaccharides produced by the hydrolysis of inulin.

2. The method of claim 1 wherein the composition additionally comprises a probiotic bacterial strain.

3. The method of claim 2, wherein the probiotic bacterial strain is *Lactobacillus rhamnosus* CGMCC 1.3724.

4. A method for reducing the risk of development of overweight or obesity in a baby, the method comprising administering a daily dose of a composition comprising 100 to 500 mg of docosahexaenoic acid to a pregnant woman in need thereof in at least the third trimester of pregnancy, wherein the composition comprises a fat source that provides 5 % to 40 % of the energy of the composition and a carbohydrate source that provides 40 % to 80 % of the energy of the composition, the composition further comprising from 2 to 8 g of dietary fiber per daily dose.

5. The method of claim 4, wherein the dietary fibre is a mixture of short and long chain fructo-oligosaccharides produced by the hydrolysis of inulin.

6. The method of claim 4, wherein the composition comprises a micronutrient selected from the group consisting of 300 to 500 mg calcium, 50 to 100 mg magnesium, 150 to 250 mg phosphorus, 5 to 20 mg iron, 1 to 7 mg zinc, 0.1 to 0.3 mg copper, 50 to 200 μg iodine, 5 to 15 μg selenium, 1000 to 3000 μg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 μg Vitamin B12, 100 to 800 μg folic acid, 30 to 70 μg biotin, 1 to 5 μg Vitamin D, and 3 to 10 IU Vitamin E.

7. The method of claim 4, wherein the composition additionally comprises a probiotic bacterial strain.

8. The method of claim 7, wherein the probiotic bacterial strain is Lactobacillus rhamnosus CGMCC 1.3724.

\* \* \* \* \*